United States Patent
Carpenter et al.

(10) Patent No.: US 7,805,174 B2
(45) Date of Patent: Sep. 28, 2010

(54) IMPLANTABLE ELECTRO-OPTICAL SENSOR

(75) Inventors: Greg Paul Carpenter, Centerville, MN (US); Michael A. Knipfer, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 191 days.

(21) Appl. No.: 11/856,850

(22) Filed: Sep. 18, 2007

(65) Prior Publication Data
US 2009/0076353 A1    Mar. 19, 2009

(51) Int. Cl.
*A61B 5/1455* (2006.01)
(52) U.S. Cl. ...................................... 600/310
(58) Field of Classification Search .................. 600/310, 600/322, 325, 333, 339, 341; 607/22, 36
See application file for complete search history.

(56) References Cited

U.S. PATENT DOCUMENTS

| | | | |
|---|---|---|---|
| 5,275,171 | A | 1/1994 | Barcel |
| 5,556,421 | A | 9/1996 | Prutchi et al. |
| 5,902,326 | A * | 5/1999 | Lessar et al. ............... 607/36 |
| 6,343,223 | B1 * | 1/2002 | Chin et al. ................. 600/323 |
| 6,491,639 | B1 | 12/2002 | Turcott |
| 7,447,533 | B1 | 11/2008 | Fang et al. |
| 2004/0100376 | A1 | 5/2004 | Lye et al. |
| 2004/0161853 | A1 | 8/2004 | Yang et al. |
| 2004/0176669 | A1 * | 9/2004 | Colvin, Jr. ................ 600/316 |
| 2004/0180391 | A1 | 9/2004 | Gratzl et al. |
| 2005/0070768 | A1 | 3/2005 | Zhu et al. |
| 2005/0221276 | A1 | 10/2005 | Rozakis et al. |
| 2005/0221277 | A1 * | 10/2005 | Kawanishi ..................... 435/4 |
| 2006/0025748 | A1 | 2/2006 | Ye |

FOREIGN PATENT DOCUMENTS

WO    WO-0025862    5/2000

(Continued)

OTHER PUBLICATIONS

Kane, Michael J. et al., "Implantable Medical Device Header with Optical Interface", U.S. Appl. No. 11/533,948.

(Continued)

*Primary Examiner*—Eric F Winakur
*Assistant Examiner*—Etsub D Berhanu
(74) *Attorney, Agent, or Firm*—Pauly, Devries Smith & Deffner, L.L.C.

(57) ABSTRACT

Embodiments of the invention are related to electro-optical implantable sensors, amongst other things. In an embodiment, the invention includes an implantable medical device including a housing defining an interior volume, the housing comprising a housing wall and defining an aperture. The implantable medical device can include an optical sensor assembly coupled to the housing wall. The optical sensor assembly can occlude the aperture in the housing wall. The optical sensor assembly can include an electro-optical module including an optical excitation assembly and an optical detection assembly. The optical sensor assembly can also include a chemical sensing element configured to detect a physiological analyte by exhibiting a change in optical properties. An optical window can be disposed between the electro-optical module and the chemical sensing element. The optical window can be configured to allow the transmission of light between the electro-optical module and the chemical sensing element. Other embodiments are also included herein.

20 Claims, 11 Drawing Sheets

FOREIGN PATENT DOCUMENTS

WO  WO-2004/071291  8/2004
WO  WO-2004/092713  10/2004

OTHER PUBLICATIONS

Kane, Michael J. et al., "Implantable Medical Device with Chemical Sensor and Related Methods", U.S. Appl. No. 11/383,926.

Kane, Michael J. et al., "Implantable Medical Device with Chemical Sensor and Related Methods", U.S. Appl. No. 11/383,933.

Koronczi, Ilona et al., "Development of Submicron Optochemical Potassium Sensor with Enhanced Stability due to Internal Reference", *Sensors and Actuators B* 51 1998, 188-195.

* cited by examiner

IMPLANTABLE ELECTRO-OPTICAL SENSOR

TECHNICAL FIELD

This disclosure relates generally to implantable sensors and, more particularly, to electro-optical implantable sensors, amongst other things.

BACKGROUND OF THE INVENTION

Certain physiological analytes are relevant to the diagnosis and treatment of medical problems. As one example, potassium ion concentrations can affect a patient's cardiac rhythm. Therefore, medical professionals frequently evaluate physiological potassium ion concentration when diagnosing cardiac rhythm problems. However, measuring physiological concentrations of analytes, such as potassium, generally requires drawing blood from the patient followed by analysis with in vitro techniques. Blood draws generally require the patient to physically visit a medical facility, such as a hospital or clinic. As a result, despite their medical significance, physiological analyte concentrations are frequently measured less often than desired due to patient discomfort and inconvenience.

One solution to these issues is to use an implanted sensor to measure physiological concentrations of analytes of interest. As such, significant efforts have been directed at the development of suitable implantable sensors. However, chronic implantable sensors present unique design issues. As such, a need remains for implantable sensors that can be used either as standalone devices or in conjunction with other implanted or external medical devices.

SUMMARY OF THE INVENTION

Embodiments of the invention are related to electro-optical implantable sensors, amongst other things. In an embodiment, the invention includes an implantable medical device including a housing defining an interior volume, the housing comprising a housing wall and defining an aperture. The implantable medical device can include an optical sensor assembly coupled to the housing wall. The optical sensor assembly can occlude the aperture in the housing wall. The optical sensor assembly can include an electro-optical module including an optical excitation assembly and an optical detection assembly. The optical sensor assembly can also include a chemical sensing element configured to detect a physiological analyte by exhibiting a change in optical properties. The optical sensor assembly can also include an optical window disposed between the electro-optical module and the chemical sensing element. The optical window can be configured to allow the transmission of light between the electro-optical module and the chemical sensing element.

In an embodiment, the invention includes an optical sensor assembly for an implantable medical device. The assembly including an optical window including edges and a flange surrounding the edges of the optical window forming a hermetic seal between the flange and the optical window. An electro-optical module can be aligned with the optical window, the electro-optical module can include an optical excitation assembly and an optical detection assembly. The optical sensor assembly can also include a chemical sensing element configured to detect a physiological analyte by exhibiting an optically detectable response to the physiological analyte. The optical window can be disposed between the electro-optical module and the chemical sensing element.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

Figure 1:
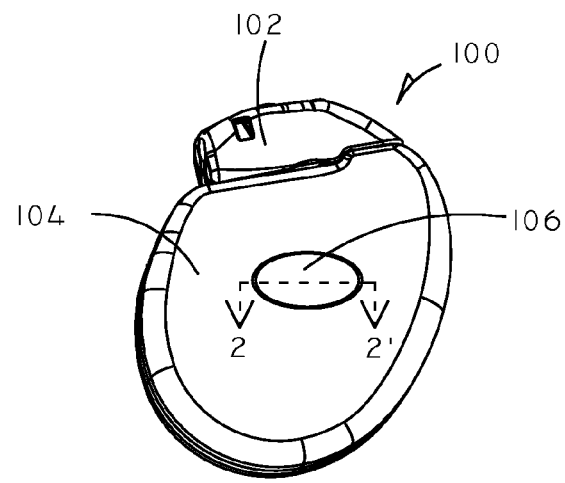
FIG. 1 is a schematic perspective view of an implantable medical device in accordance with an embodiment of the invention.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Physiological analyte concentrations are important data points for both the diagnosis and treatment of many medical problems. For example, knowledge of potassium ion concentrations can be important to the correct diagnosis of cardiac arrhythmias. Likewise, the concentrations of other physiological ions, such as sodium and calcium, can also be important in the diagnosis and treatment of cardiac arrhythmias.

Beyond cardiac rhythm problems, analyte sensing can also be useful in the context of monitoring drug therapy, monitoring renal function, titrating drugs (such as hearth failure medications), monitoring for heart failure decompensation, and observing primary electrolyte imbalance subsequent to dietary intake or renal excretion variations, amongst other uses.

The use of implantable sensors for assessing physiological analyte concentrations can be a particularly valuable approach because data can be gathered as often as desired without inconveniencing the patient. In addition, the use of an implantable sensor offers the advantage of being able to gather data in real time.

However, implantable sensor systems pose various design issues. Such issues include a desire to protect sensitive electronic components within a hermetically sealed environment while also preventing contact of potentially non-biocompatible materials with tissues of the subject. Design issues can be particularly acute in the context of electro-optical implantable sensors. From the perspective of robust design, some of the electro-optical components, such as a light source and a light detector, are desirably included inside of a housing where they are protected in a hermetically sealed environment and can be efficiently integrated with other electronic components therein. However, from the perspective of sensitivity of detection, it can be advantageous to have other components of the sensor located outside of the housing, in contact with bodily fluids.

Embodiments of the invention can allow certain components of the sensor, such as the light source and the light detector, to remain protected within a hermetically sealed environment while placing other components of the sensor, such as a chemical sensing element, in contact with bodily fluids. Specifically, embodiments of the invention can include an implantable medical device with an optical window, wherein the optical window is used to maintain the hermeticity of the inside of the medical device housing. In various embodiments, an electro-optical module, including an optical excitation assembly and an optical detection assembly, can be disposed on the inside of the optical window in a hermetically sealed environment, while a chemical sensing element can be disposed on the outside the optical window in contact with bodily fluids. The chemical sensing element can be configured to detect a physiological analyte by exhibiting an optically detectable response to the physiological analyte. The optically detectable response can be detected by the electro-optical module located inside of the medical device housing. This configuration offers various advantages including the ability to keep the relatively sensitive electro-optical components within the protected environment inside of the medical device housing while keeping the chemical sensing element outside of the housing facilitating interaction with a desired analyte in vivo.

Referring now to FIG. 1, a schematic perspective view is shown of an implantable medical device 100 in accordance with an embodiment of the invention. The implantable medical device 100 includes a housing 104 (or can) and a header assembly 102 coupled to the housing 104. The housing 104 can include various materials such as metals, polymers, ceramics, and the like. In a particular embodiment, the housing 104 is formed of titanium. The header assembly 102 serves to provide fixation of the proximal end of one or more leads (not shown) and electrically couples the leads to components within the housing 104. The header assembly 102 can be formed of various materials including metals, polymers, ceramics, and the like. The implantable medical device 100 also includes an optical sensor assembly 106.

Figure 2:
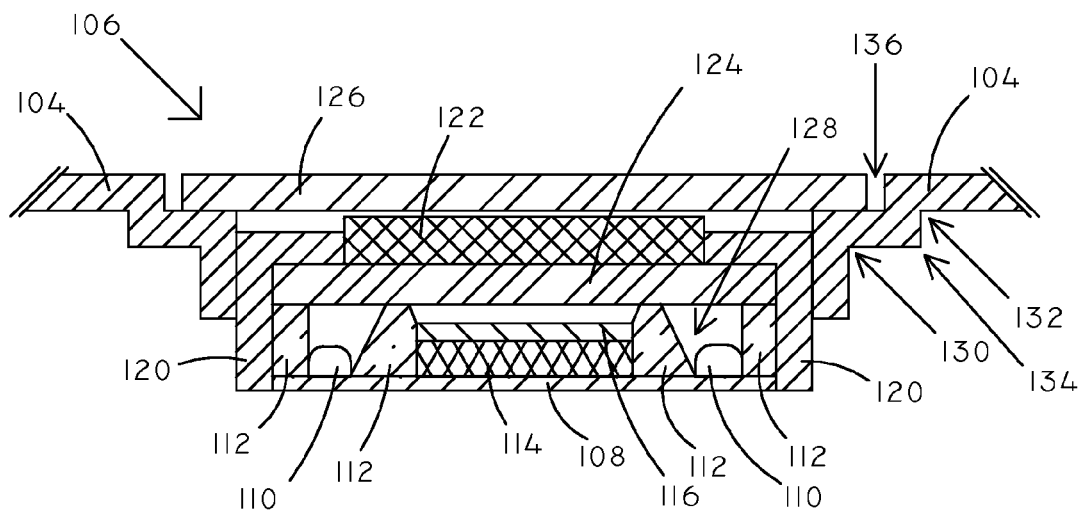
FIG. 2 is a schematic cross-sectional view of an optical sensor assembly shown as taken along line 2-2' of FIG. 1.

Referring now to FIG. 2, a cross-sectional view of an optical sensor assembly 106 is shown as taken along line 2-2' of FIG. 1. The optical sensor assembly 106 can include an optical window 124 coupled to a flange 120. In some embodiments, the optical window 124 can be substantially rigid. However, in other embodiments, the optical window 124 can be flexible. In some embodiments, the optical window 124 can be planar. The optical window 124 can be configured to allow the transmission of light. Various materials can be used to form the optical window 124 including crystal, glass, ceramics, polymers, and the like. In some embodiments, the optical window 124 can include sapphire. In some embodiments, the optical window 124 can include polyurethane. In various embodiments, the optical window 124 can be made of a biocompatible material.

In some embodiments, the optical window 124 can be configured to block the transmission of certain wavelengths of electromagnetic radiation. By way of example, the optical window 124 material can be configured to filter out infrared light in some embodiments. In other embodiments, the optical window 124 can be covered with a layer of filter material that blocks the transmission of certain wavelengths of electromagnetic radiation, such as infrared light. In some embodiments, the surfaces of the optical window 124 can be provided with an anti-reflection coating in order to reduce optical loss when transmitting light through the window.

The flange 120 can surround the edges of the optical window 124 forming a hermetic seal between the flange 120 and the optical window 124. The flange 120 can include various metals such as titanium, platinum, chromium, gold, various alloys, and the like. The flange 120 can be attached to the optical window 124 using various techniques including brazing, soldering, use of an adhesive, use of a press fitting, or the like.

The flange 120 can be coupled to the housing 104 of the implantable medical device 100 of FIG. 1 in a hermetically sealing manner. For example, the flange 120 can be welded to the housing 104 of the implantable medical device 100. In other embodiments, the flange 120 can be adhesively bonded to the housing 104, such as with an epoxy adhesive. Alternatively, the flange 120 can be soldered or brazed to the housing 104. In some embodiments, a press fitting can be used between the flange 120 and the housing 104. In such various ways, a hermetic seal in the area of the optical sensor assembly 106 on the device 100 can be formed through the interaction of the housing 104, the flange 120, and the optical window 124.

As can be seen, the housing 104 defines an aperture into which the optical sensor assembly 106 fits. In some embodiments, the housing 104 can define a stepped flange 134 with one or more steps 130, 132 around the aperture. The stepped flange 134 can define a recessed portion 136. In some embodiments, the stepped flange 134 can be made of the same material as the housing 104. For example, the flange 134 can be made by machining, coining, stamping, deep drawing, or another similar technique. In other embodiments, the stepped flange 134 can be made of a material different than the material of the housing 104. It will be appreciated that various flange profiles can be used to compensate for potentially differing coefficients of thermal expansion (CTE) and mechanical stiffness of the window, flange, and housing materials.

The optical sensor assembly 106 can include an electro-optical module 128 coupled to the optical window 124. The electro-optical module 128 can specifically include one or more optical excitation assemblies 110. Each optical excitation assembly 110 can include various emitters of light such as light-emitting diodes (LEDs), vertical-cavity surface-emitting lasers (VCSELs), electroluminescent (EL) devices or the like. The electro-optical module 128 can also include one or more optical detection assemblies 114. Each optical detection assembly 114 can include one or more photodiodes, avalanche photodiodes, a photodiode array, a photo transistor, a multi-element photo sensor, a CMOS photo sensor, or the like. In some embodiments, an optical filter 116 can be disposed over the optical detection assembly 114. The optical filter 116 can be configured to pass only certain wavelengths of light. By way of example, the optical filter 116 can be configured to pass only a band of light needed for use with a chemical sensing element. In some embodiments, the optical filter 116 may be coated differently across its surface to allow variable wavelength transmission across its surface.

In some embodiments, the electro-optical module 128 can optionally include an optical shroud 112. The optical shroud 112 can serve to optically isolate the optical detection assembly(s) 114 and the optical excitation assembly(s) 110 from one another. The optical shroud 112 can also be configured to mirror, focus, or direct light as an optical alignment fixture.

In some embodiments, the electro-optical module 128 can also include a substrate 108, upon which other components of the electro-optical module 128 can be mounted. The substrate 108 can be configured so that it does not conduct or pipe light between the optical excitation assembly(s) 110 and the optical detection assembly(s) 114. This can be accomplished in various ways such as by including or cutting voids in the substrate such that no direct light path exists between optical excitation assemblies and optical detection assemblies. In some embodiments, the electro-optical module 128 can be configured to fit within a recess defined by the flange 120 and the optical window 124.

A chemical sensing element 122 can be disposed on the optical window 124. The chemical sensing element 122 can be configured to detect a physiological analyte by exhibiting an optically detectable response to the physiological analyte. Various aspects of exemplary chemical sensing elements are described in greater detail below.

In some embodiments, a biocompatible cover layer 126 can be disposed over the chemical sensing element 122. The cover layer 126 can be permeable to an analyte of interest allowing the analyte to diffuse through the cover layer 126 and into contact with the optical chemical sensing element 122. The cover layer 126 can be configured to protect the chemical sensing element 122 from damage during the manufacturing process and during implantation of the device. The cover layer 126 can also serve optical functions. By way of example, the cover layer 126 can block ambient light. In some embodiments, the cover layer 126 can also prevent light from escaping the medical device. In some embodiments, the cover layer 126 can be configured to diffusely reflect light back into the chemical sensing element 122. In some embodiments, the cover layer 126 can include optical path calibration features such as a known fluorescent or calorimetric indicator.

In some embodiments, the cover layer 126 can be configured to prevent the in-growth of tissue. Various materials can be used to form the cover layer 126. In some embodiments, the cover layer 126 is a porous polymeric material. In some embodiments, the cover layer 126 is polytetrafluoroethylene (PTFE). In some embodiments, the cover layer 126 can be disposed within the recessed portion 136 of the stepped flange 134. In some embodiments, the cover layer 126 can be flush with the outer surface of the housing 104. However, in other embodiments, the cover layer 126 is not flush with the outer surface of the housing 104.

Figure 3:
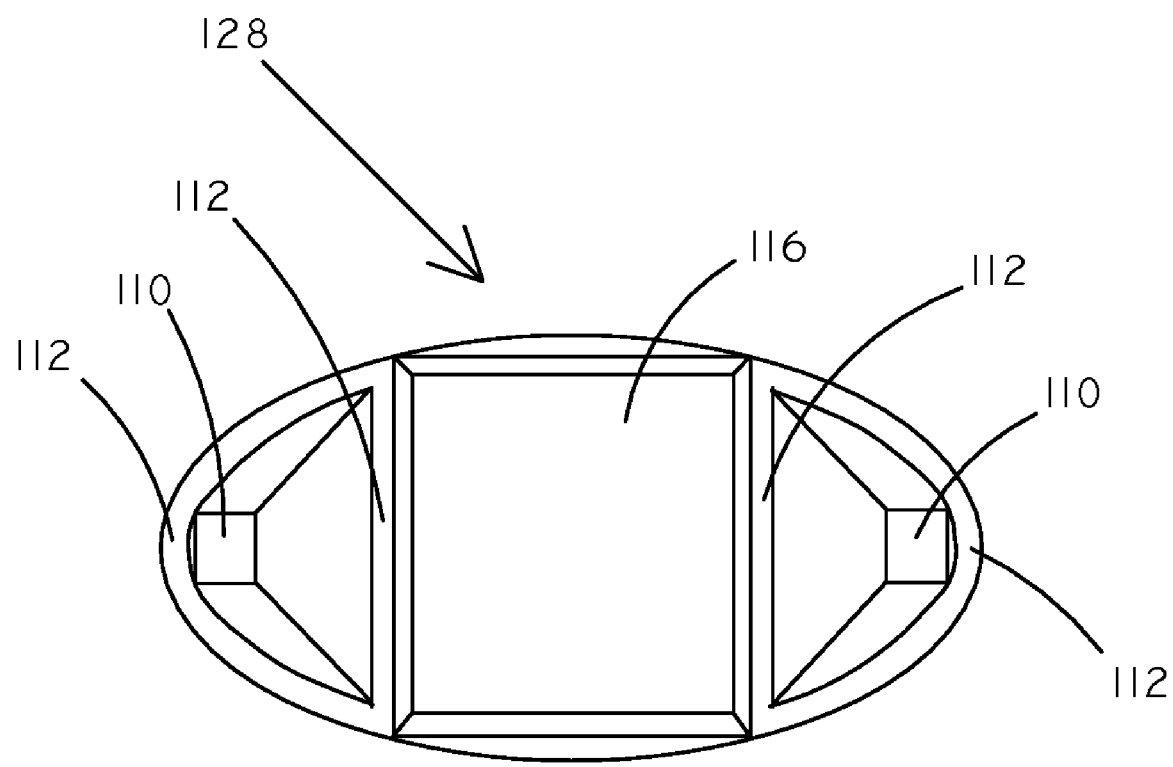
FIG. 3 is a schematic top view of an electro-optical module in accordance with an embodiment of the invention.

Referring now to FIG. 3, a top schematic view is shown of the electro-optical module 128. In this view, the optical shroud 112 is shown surrounding the optical excitation assembly units 110. Though two optical excitation assembly units 110 are shown in this view, it will be appreciated that in some embodiments only one optical excitation assembly unit may be included. In still other embodiments, a number of optical excitation assembly units greater than two can be included, such as an array of optical excitation assembly units. This view further shows the optical filter 116 disposed over the optical detection assembly 114.

The electro-optical module 128 of FIG. 3 is shown in an oval configuration. The optical window 124 (shown in FIG. 2) can also take on an oval configuration. In various other embodiments, the electro-optical module and the optical window can take on other shapes such as a circular shape or a polygonal shape with rounded edges. While not intending to be bound by theory it is believed that shapes without sharp edges can be advantageous because of various reasons including a reduction in stresses, ease of hermetic sealing, and the like.

Figure 4:
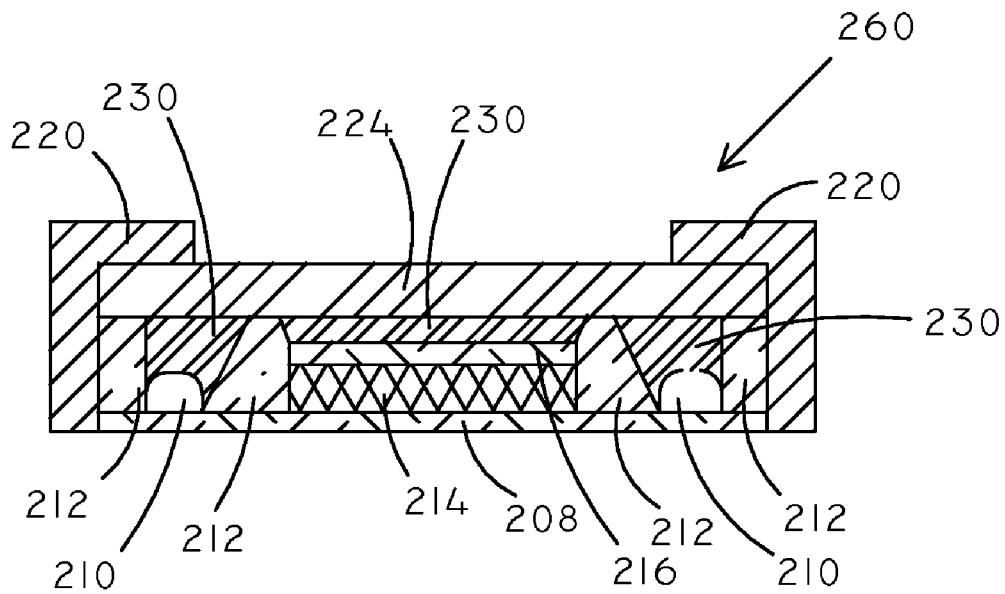
FIG. 4 is a schematic cross-sectional view of an optical sensor assembly in accordance with an embodiment of the invention.

In some embodiments, an encapsulant can be disposed over components of the electro-optical module. The encapsulant can serve various purposes including filtering out background light and providing structural integrity to the electro-optical module. Referring now to FIG. 4, a cross-sectional view of an optical sensor assembly 260 is shown in accordance with an embodiment of the invention. The optical sensor assembly 260 can include a flange 220 coupled to an optical window 224. The optical sensor assembly 260 can also include an electro-optical module including a substrate 208, optical excitation assemblies 210, optical detection assembly 214, and an optical filter 216 disposed over the optical detection assembly 214. The electro-optical module can also include an optical shroud 212. An encapsulant 230 can be disposed over the components of the electro-optical module including the optical excitation assembly(s) 210 and the optical detection assembly(s) 214. The encapsulant 230 can serve to provide structure integrity to the electro-optical module. The encapsulant 230 can also be configured to block certain wavelengths of light that may serve as a contaminant, such as infrared light. In some embodiments, the encapsulant 230 can include a polymeric material, such as epoxy, with a dye to filter out infra-red light. In some embodiments, the encapsulant 230 can contain titanium dioxide to aid in diffusing light. In some cases, the optical window 224 can be formed with the same material as the encapsulant 230, and the two components can be integral.

In some embodiments, the electro-optical module can be configured so that it fits within the flange of the optical sensor assembly in only a single orientation. By way of example, the electro-optical module and the flange of the optical sensor assembly can include complementary structural features configured so that they fit together similar to a lock and key. This can provide advantages during the assembly process, such as easier assembly and potentially reducing the number of manufacturing defects resulting from the electro-optical module being improperly aligned with the optical window.

Figure 5:
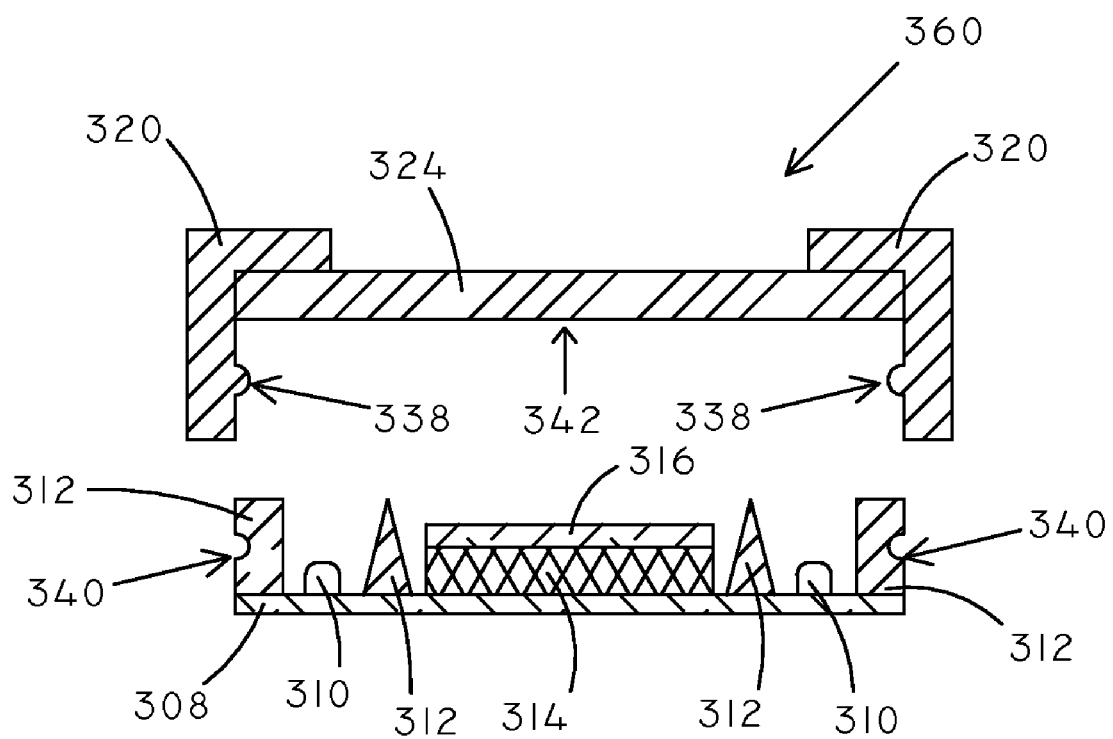
FIG. 5 is a partially exploded schematic cross-sectional view of an optical sensor assembly in accordance with an embodiment of the invention.

Referring now to FIG. 5, a partially exploded cross-sectional view of an optical sensor assembly 360 is shown in accordance with another embodiment of the invention. The optical sensor assembly 360 includes a flange 320 coupled to an optical window 324. The optical sensor assembly 360 can also include an electro-optical module including a substrate 308, optical excitation assemblies 310, optical detection assembly 314, and an optical filter 316 disposed over the optical detection assembly 314. The electro-optical module can also include an optical shroud 312.

The flange 320 can include first structural features 338 that are complementary to second structural features 340 on the electro-optical module. The electro-optical module can be fitted into the flange 320 by moving it in the direction of arrow 342. The first structural features 338 and the second structural features 340 can fit together in a manner so as to allow for a single orientation between the flange and the electro-optical module. It will be appreciated that the structural features 338 and 340 can take on many different forms. In some embodiments, the structural features 338 and 340 can form a compression fitting or snap fitting that also serves to retain the electro-optical module within the flange 320.

Figure 6:
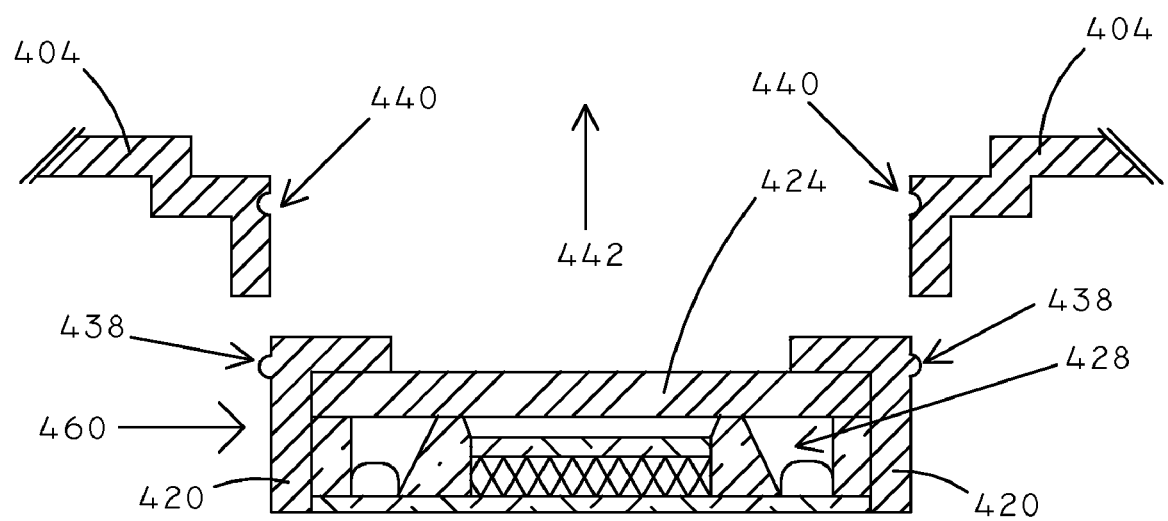
FIG. 6 is a partially exploded schematic cross-sectional view of an optical sensor assembly in accordance with an embodiment of the invention.

FIG. 6 is a partially exploded cross-sectional view of an optical sensor assembly 460 shown in accordance with another embodiment of the invention. The optical sensor assembly 460 includes a flange 420 coupled to an optical window 424. The optical sensor assembly 460 can also include an electro-optical module 428. The flange 420 can include first structural features 438 that are complementary to second structural features 440 on the wall member 404 of the housing. The optical sensor assembly 460 and the wall member 404 can fit together such as by the optical sensor assembly 460 moving in the direction of arrow 442 with respect to the wall member 404. The first structural features 438 and the second structural features 440 can fit together in a manner so as to allow for a single orientation between the wall member 404 and the optical sensor assembly 460. It will be appreciated that the structural features 438 and 440 can take on many different forms. In some embodiments, the structural features 438 and 440 can form a compression fitting or snap fitting that also serves to couple the optical sensor assembly 460 to the wall member 404.

Figure 7:
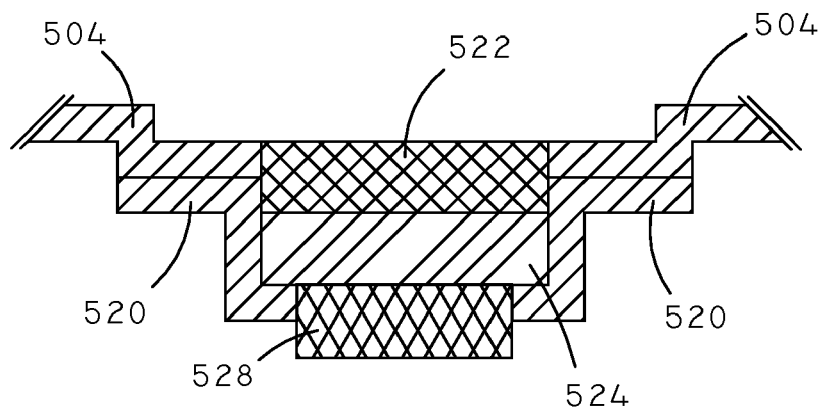
FIG. 7 is a schematic cross-sectional view of an optical sensor assembly in accordance with an embodiment of the invention.

It will be appreciated that many different specific configurations of the optical sensor assembly are contemplated herein. Referring now to FIG. 7, a schematic cross-sectional view of an optical sensor assembly is shown in accordance with another embodiment of the invention. The optical sensor assembly includes a flange 520 coupled to an optical window 524. The flange 520 can be coupled to the housing 504 of an implantable medical device. A chemical sensing element 522 can be disposed on top of the optical window 524 and an electro-optical module 528 can be disposed below the optical window 524. In operation, analytes of interest from the in vivo environment can diffuse into the chemical sensing element 522 causing a detectable change in the optical properties of the chemical sensing element 522. Light can be generated by the electro-optical module 528 and can pass through the optical window 524 and into the chemical sensing element 522. Light can then either be preferentially reflected by or re-emitted by the chemical sensing element 522 proportional to the sensed analyte and pass back through the optical window 524 before being received by the electro-optical module 528.

Figure 8:
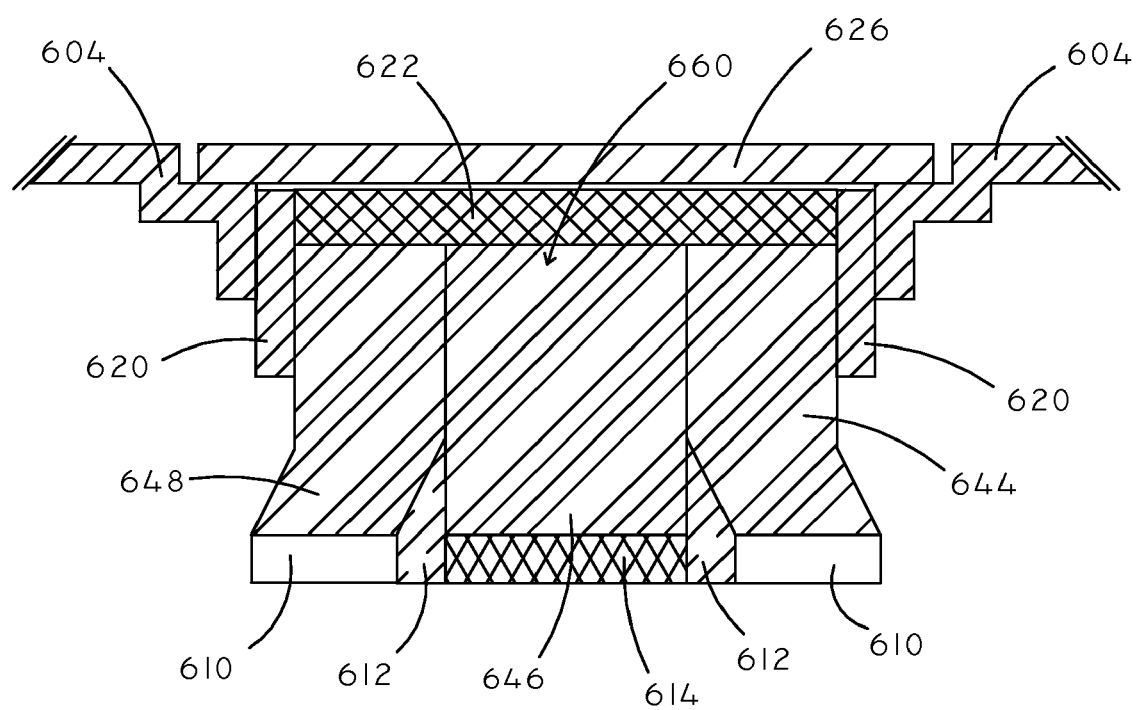
FIG. 8 is a schematic cross-sectional view of an optical sensor assembly in accordance with an embodiment of the invention.

Referring now to FIG. 8, a cross-sectional view of a optical sensor assembly is shown in accordance with another embodiment of the invention. The optical sensor assembly includes a flange 620 coupled to a window assembly 660. The window assembly 660 includes light guides 644, 646, 648 coupled together in a manner so as to maintain hermeticity within the interior of the housing 604. Light guide 644 is configured to convey light from an optical excitation unit 610 to the chemical sensing element 622. Similarly, light guide 648 is configured to convey light from an optical excitation unit 610 to the chemical sensing element 622. Light guide 646 is configured to convey light from the chemical sensing element 622 to the optical detection assembly 614. Optical shroud 612 serves to optically isolate the optical excitation assembly units 610 from the optical detection assembly 614. A cover 626 can be disposed over the chemical sensing element 622.

Figure 9:
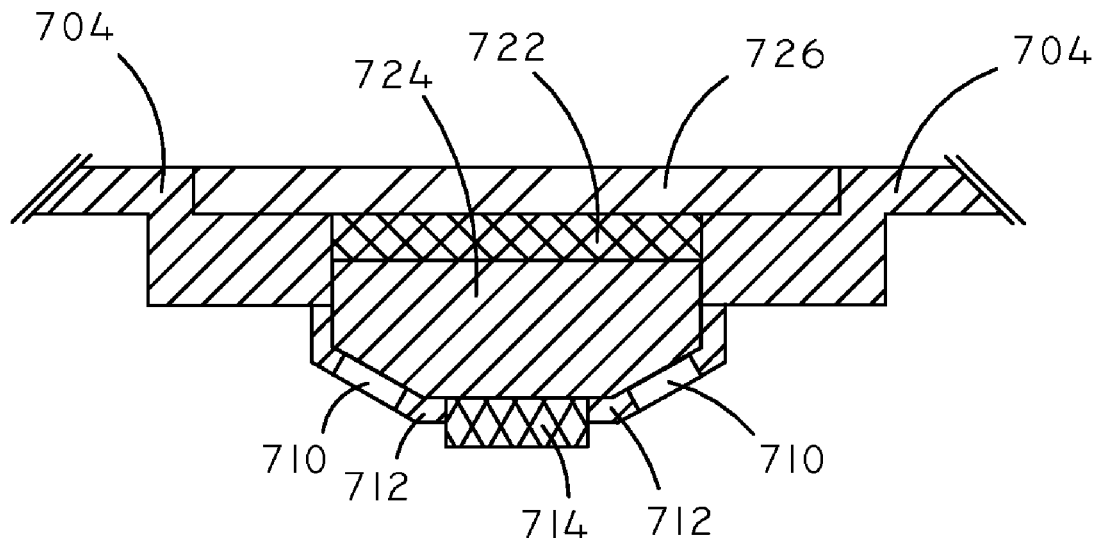
FIG. 9 is a schematic cross-sectional view of an optical sensor assembly in accordance with an embodiment of the invention.

Referring now to FIG. 9, a cross-sectional view of an optical sensor assembly is shown in accordance with another embodiment of the invention. The optical sensor assembly includes an optical window 724 disposed below a chemical sensing element 722. The optical window 724 is coupled to the housing 704 of an implantable medical device in a manner so as to from a hermetic seal between the housing 704 and the optical window 724. An electro-optical module is disposed below the optical window 724 including optical excitation assembly units 710 and an optical detection assembly 714. Optical shroud 712 serves to optically isolate the optical excitation assembly units 710 from the optical detection assembly unit 714. The optical sensor assembly further includes a cover 726 disposed over the chemical sensing element 722.

Figure 10:
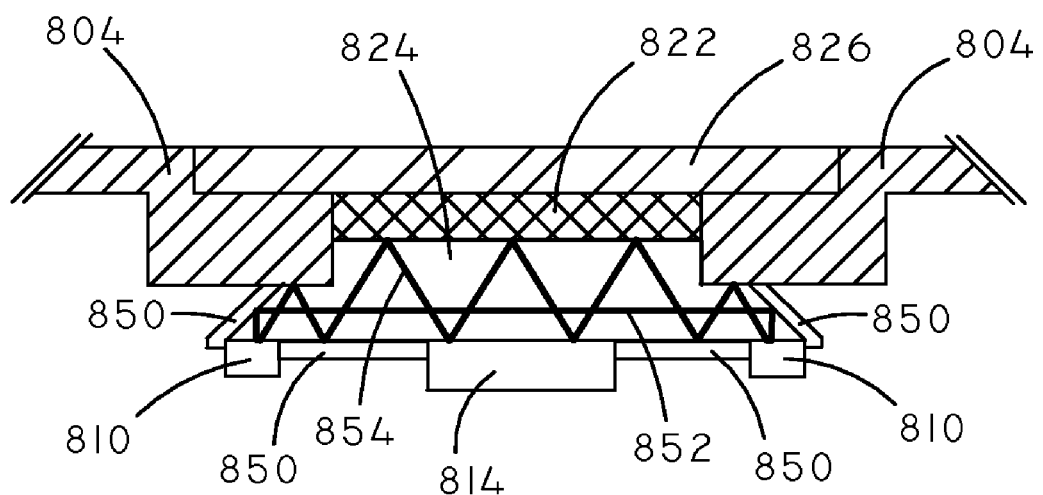
FIG. 10 is a schematic cross-sectional view of an optical sensor assembly in accordance with an embodiment of the invention.

Referring now to FIG. 10, a cross-sectional view of an optical sensor assembly is shown in accordance with another embodiment of the invention. The optical sensor assembly includes an optical window 824 disposed below a chemical sensing element 822. A reflector 850 is shown disposed along the surfaces of the optical window 824. This reflection feature can be created by specular or diffuse mirror coatings or by total internal reflection. An optical excitation/detection assembly 810 is configured to generate light as shown by paths 852 and 854. Light following reference path 852 passes from the optical excitation/detection assembly 810 directly through the optical window 824 before encountering another optical excitation/detection assembly 810. In contrast, light following sensing path 854 passes from the optical excitation/detection assembly 810 and bounces between the chemical sensing element 822 and the reflector 850 before encountering the optical detection assembly 814. The housing 804 of the medical device is coupled to the optical window 824 is a manner so as maintain the hermeticity of the interior volume of the implantable medical device. The optical sensor assembly can further include a cover 826 disposed over the chemical sensing element 822.

Figure 11:
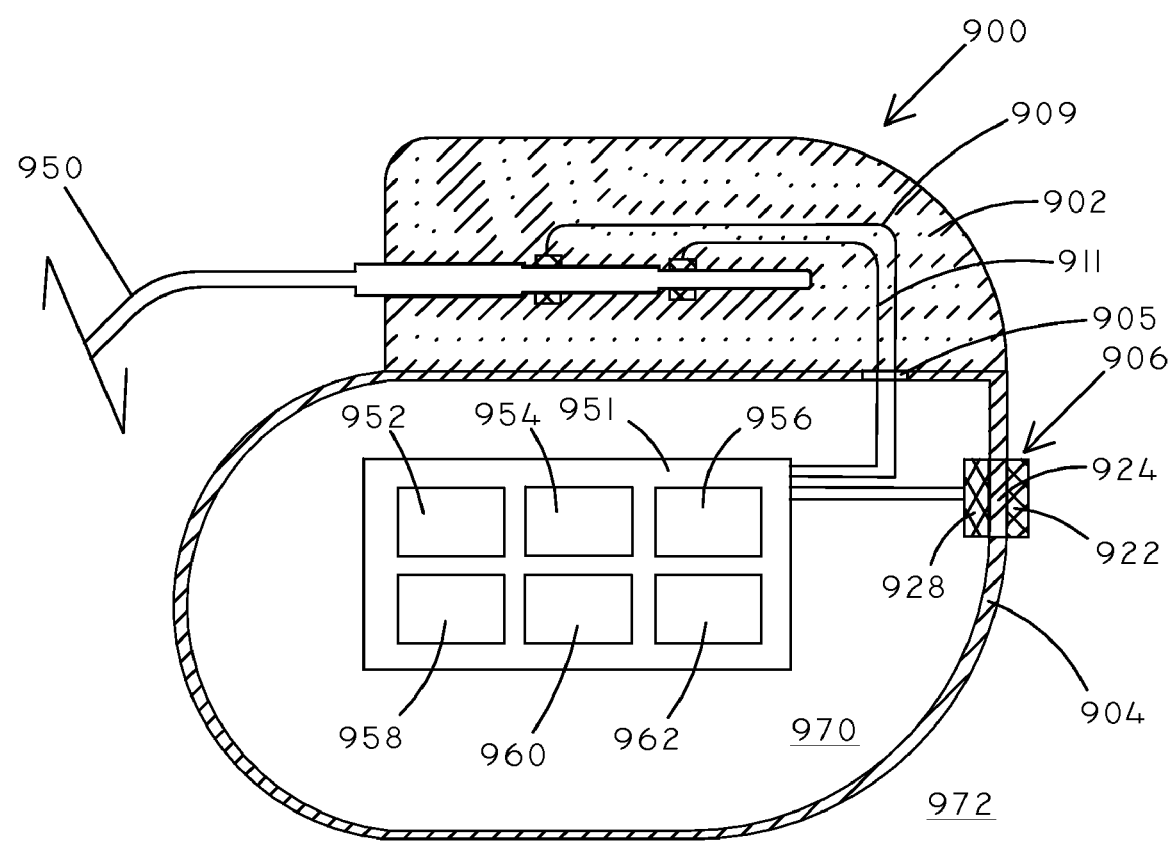
FIG. 11 is a schematic cross-sectional view of an implantable medical device in accordance with an embodiment of the invention.

It will be appreciated that optical sensor assemblies as described herein can be used in conjunction with various types of implantable medical devices. By way of example, optical sensor assemblies as described herein can be used in conjunction with cardiac rhythm management (CRM) devices configured to provide electrical stimulation therapy to a patient. Referring now to FIG. 11, a schematic cross-sectional view of an implantable medical device 900 is shown in accordance with an embodiment of the invention. The implantable medical device 900 includes a header 902 and a housing 904. The header 902 can be coupled to one or more electrical stimulation leads 950. The stimulation lead 950 can be used to deliver electrical stimulation therapy to a target tissue. The implantable medical device 900 can be a pacemaker, an implantable cardioverter-defibrillator, or the like.

The housing 904 of the implantable medical device 900 defines an interior volume 970 that is hermetically sealed off from the volume 972 outside of the device 900. Various electrical conductors 909, 911 can pass from the header 902 through a feed-through structure 905, and into the interior volume 970. As such, the conductors 909, 911 can serve to provide electrical communication between the electrical stimulation lead 950 and circuitry 951 disposed within the interior volume 970 of the housing 904. The circuitry 951 can include various components such as a microprocessor 952, memory (such as RAM and/or ROM) 954, a telemetry module 956, electrical sensing and stimulation circuitry 958, a power supply 960 (such as a battery), and an optical sensor interface channel 962, amongst others.

The implantable medical device 900 can also include an optical sensor assembly 906. The optical sensor assembly 906 can specifically include a chemical sensing element 922, an optical window 924, and an electro-optical module 928. The electro-optical module 928 can be disposed within the hermetically sealed interior volume 970 of the housing 904. The electro-optical module 928 can be in electrical communication with the circuitry 951 within the interior volume 970.

Figure 12:
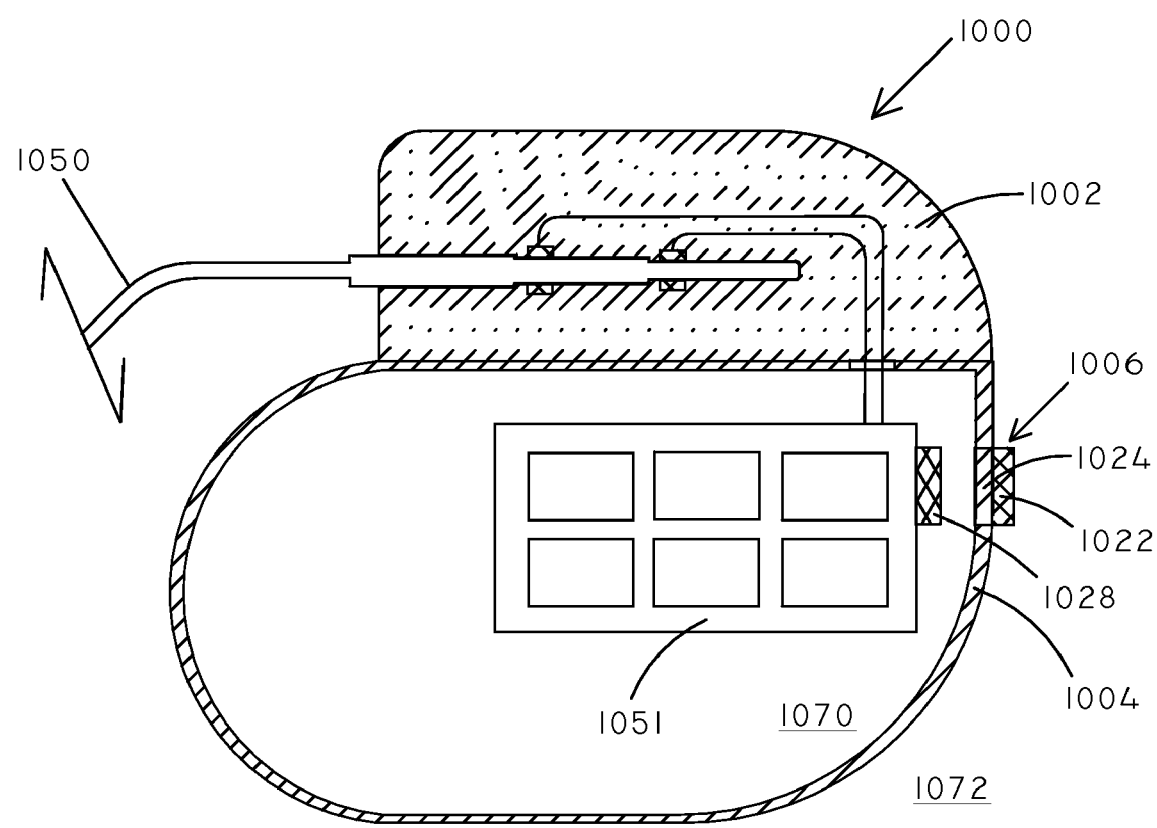
FIG. 12 is a schematic cross-sectional view of an implantable medical device in accordance with another embodiment of the invention.

It will be appreciated that in some embodiments, the electro-optical module can be located with the internal circuitry of the device, such as on the same circuit substrate, and not attached to the housing. In such an embodiment, the electro-optical module can be aligned with the optical window, but may not necessarily be in contact with the optical window. Referring now to FIG. 12, a schematic cross-sectional view of an implantable medical device 1000 is shown in accordance with an embodiment of the invention. The implantable medical device 1000 includes a header 1002 and a housing 1004. The header 1002 can be coupled to one or more electrical stimulation leads 1050. The housing 1004 of the implantable medical device 1000 defines an interior volume 1070 that is hermetically sealed off from the volume 1072 outside of the device 1000. Circuitry 1051 to operate the device can be disposed within the interior volume 1070. The implantable medical device 1000 can also include an optical sensor assembly 1006. The optical sensor assembly 1006 can specifically include a chemical sensing element 1022, an optical window 1024, and an electro-optical module 1028. The electro-optical module 1028 can be disposed along with the circuitry 1051, but aligned with the optical window 1024. The chemical sensing element 1022 can also be aligned with the optical window 1024.

Figure 13:
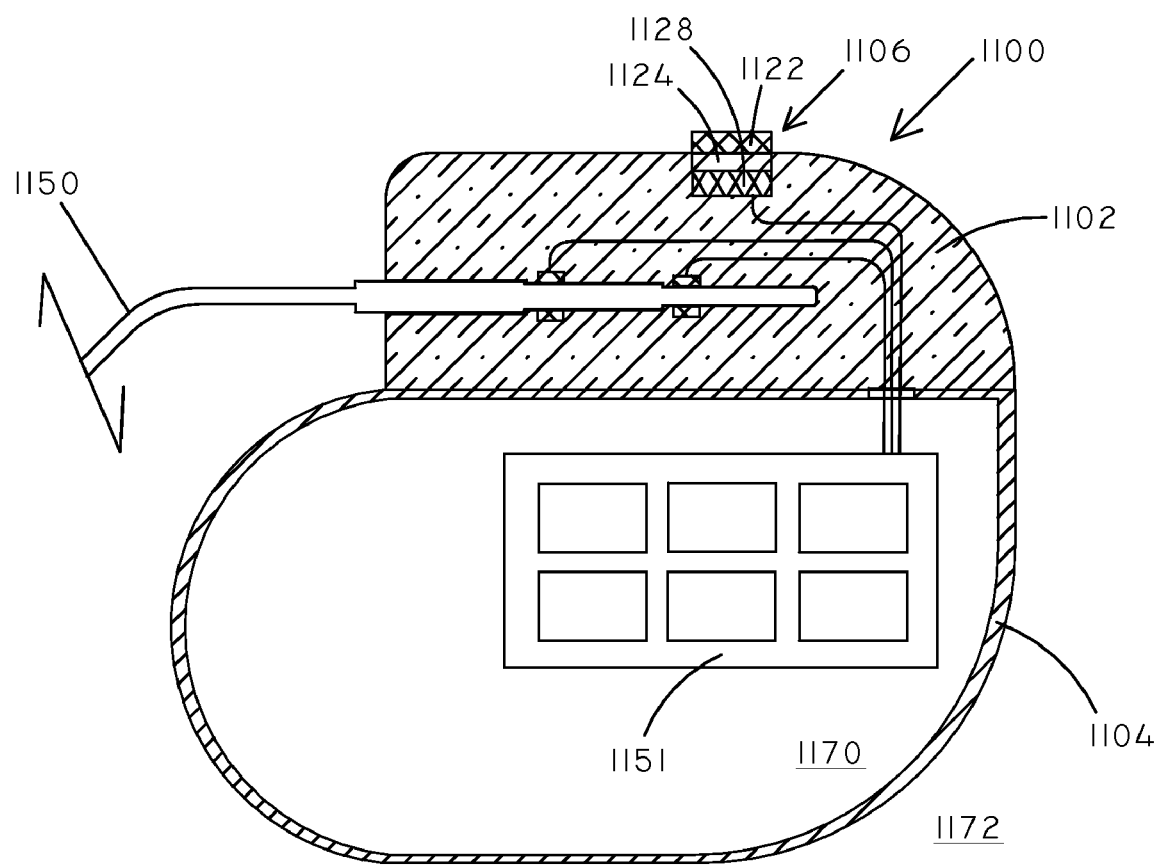
FIG. 13 is a schematic cross-sectional view of an implantable medical device in accordance with another embodiment of the invention.

In some embodiments, the optical sensor assembly can be disposed on or within the header of a device. Referring now to FIG. 13, a schematic view of an implantable medical system 1100 is shown in accordance with another embodiment of the invention. The implantable medical device 1100 includes a header 1102 and a housing 1104. The header 1102 can be coupled to one or more electrical stimulation leads 1150. The housing 1104 of the implantable medical device 1100 defines an interior volume 1170 that is hermetically sealed off from the volume 1172 outside of the device 1100. Circuitry 1151 to operate the device can be disposed within the interior volume 1170. The implantable medical device 1100 can also include an optical sensor assembly 1106 disposed within the header 11102. The optical sensor assembly 1106 can specifically include a chemical sensing element 1122, an optical window 1124, and an electro-optical module 1128.

Figure 14:
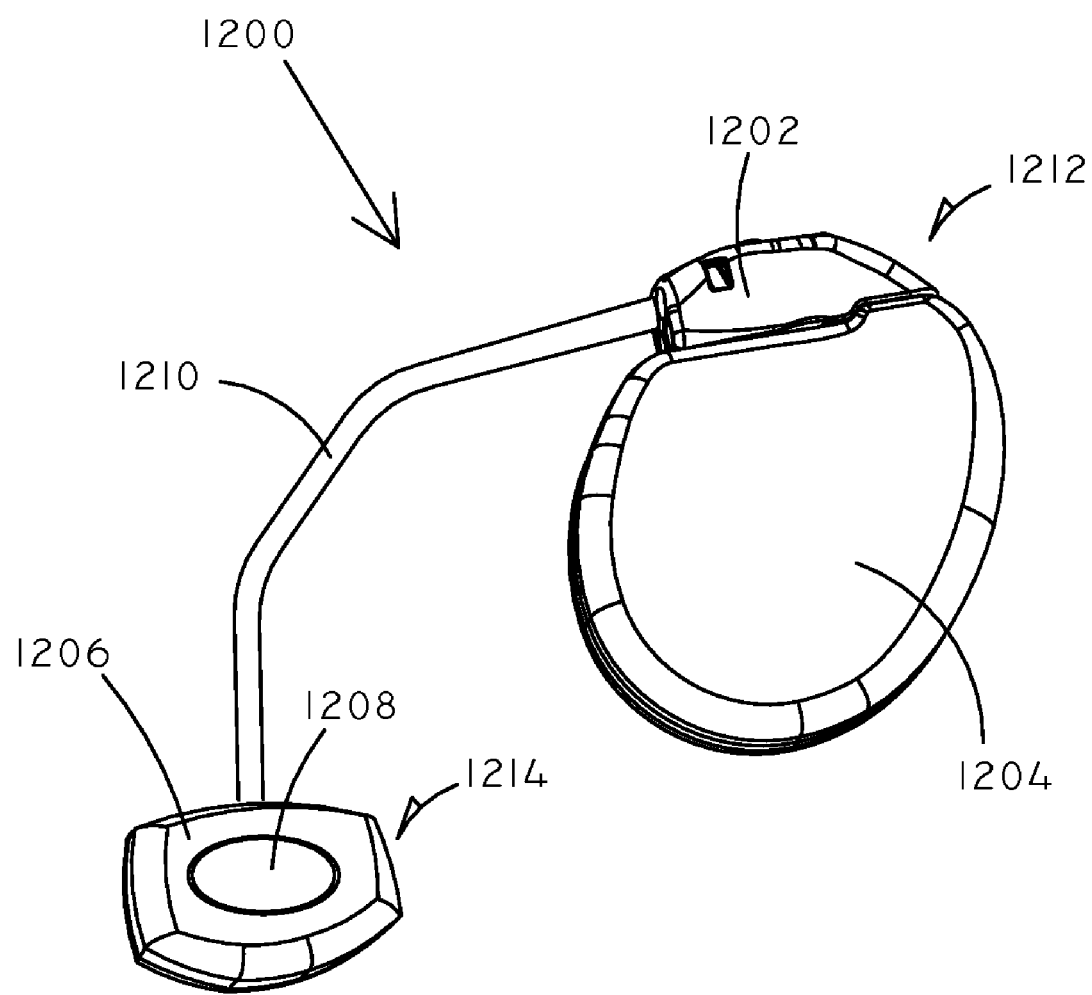
FIG. 14 is a schematic view of an implantable medical system in accordance with an embodiment of the invention.

Referring now to FIG. 14, a schematic view of an implantable medical system 1200 is shown in accordance with another embodiment of the invention. A pulse generating device 1212, including a housing 1204 is coupled to a header 1202. The pulse generating device 1212 can be, for example, a pacemaker or an implantable cardioverter-defibrillator. The header 1202 is coupled to a lead 1210 which is, in turn, coupled to a sensor device 1214. The sensor device 1214 can include a housing 1206 and an optical sensor assembly 1208. The sensor device 1214 and the pulse generating device 1212 can be in signal communication. In some embodiments, the lead 1210 can include one or more electrodes and can be an electrical stimulation lead. In some embodiments, lead 1210 can be replaced with a wireless communication and power link.

Figure 15:
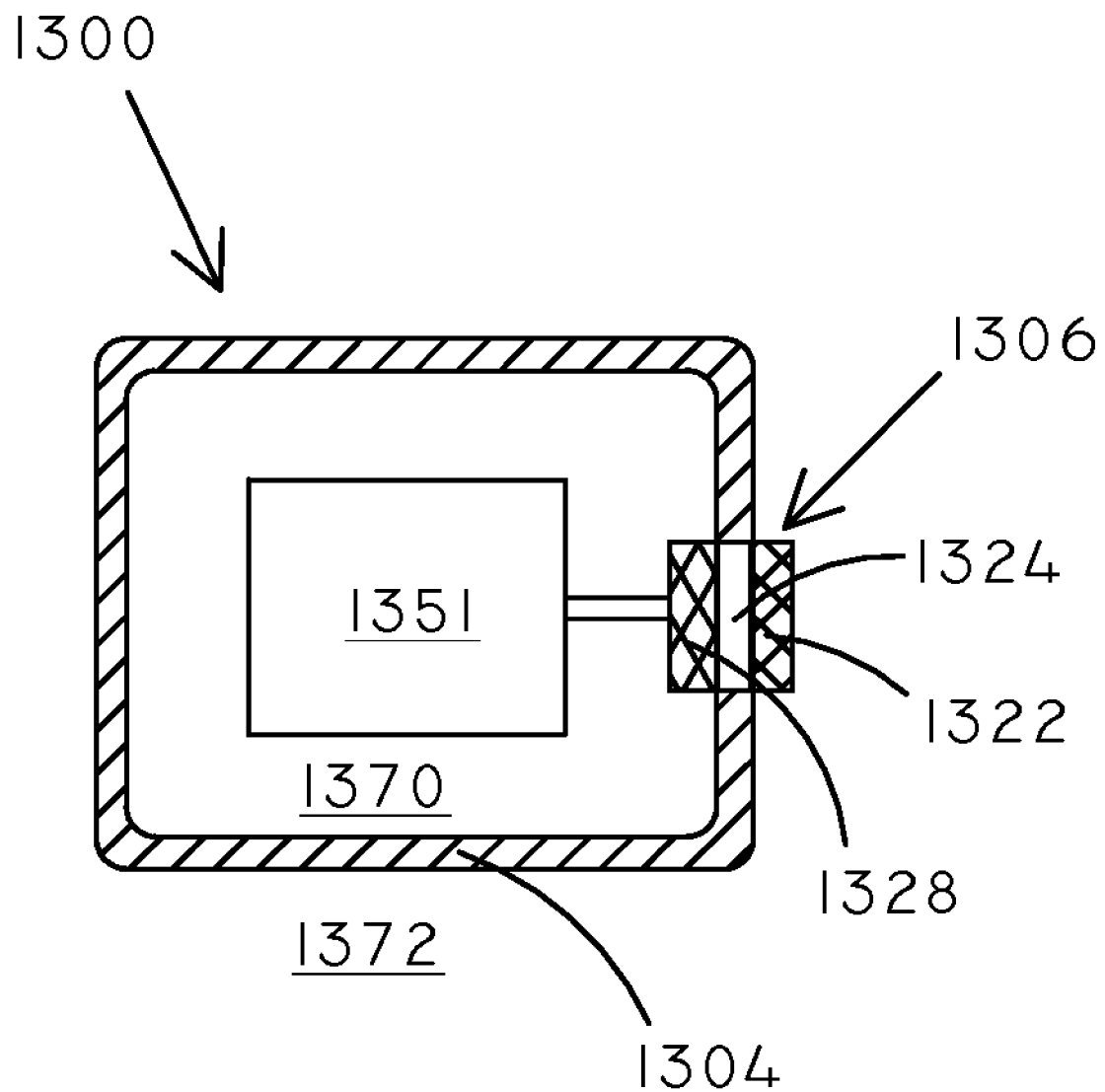
FIG. 15 is a schematic cross-sectional view of an implantable sensor in accordance with an embodiment of the invention.

While some optical sensor assemblies as described herein can be used as a part of implantable medical devices such as cardiac rhythm management (CRM) devices, it will be appreciated that optical sensor assemblies can also be used as a part of stand-alone sensor devices. Referring now to FIG. 15, a schematic cross-sectional view of a stand-alone sensor device 1300 is shown including an optical sensor assembly 1306. The sensor device 1300 includes a housing 1304 defining an interior volume 1370 that is hermetically sealed off from the volume 1372 outside of the device 1300. The optical sensor assembly 1306 includes a chemical sensing element 1322, an optical window 1324, and an electro-optical module 1328. The electro-optical module 1328 can be disposed within the hermetically sealed interior volume 1370 of the housing 1304. The electro-optical module 1328 can be in electrical communication with circuitry 1351 within the interior volume 1370. The circuitry 1351 can monitor the sensing system as well as handle power and communication functions.

It will be appreciated that in accordance with various embodiments described herein, the sensing of analyte concentrations can be directed at a specific analyte or a plurality of different analytes. In an embodiment, the analyte sensed is one or more analytes relevant to cardiac health. In an embodiment, the analyte sensed is one or more analytes indicative of renal health. The analyte sensed can be an ion or a non-ion. The analyte sensed can be a cation or an anion. Specific examples of analytes that can be sensed include, but are not limited to, acetic acid (acetate), aconitic acid (aconitate), ammonium, blood urea nitrogen (BUN), B-type natriuretic peptide (BNP), bromate, calcium, carbon dioxide, cardiac specific troponin, chloride, choline, citric acid (citrate), cortisol, copper, creatinine, creatinine kinase, fluoride, formic acid (formate), glucose, hydronium ion, isocitrate, lactic acid (lactate), lithium, magnesium, maleic acid (maleate), malonic acid (malonate), myoglobin, nitrate, nitric-oxide, oxalic acid (oxalate), oxygen, phosphate, phthalate, potassium, pyruvic acid (pyruvate), selenite, sodium, sulfate, urea, uric acid, and zinc. Inorganic cations sensed by this method include but are not limited to hydronium ion, lithium ion, sodium ion, potassium ion, magnesium ion, calcium ion, silver ion, zinc ion, mercury ion, lead ion and ammonium ion. Inorganic anions sensed by this method include but are not limited to carbonate anion, nitrate anion, sulfite anion, chloride anion, and iodide anion. Organic cations sensed by this method include but are not limited to norephedrine, ephedrine, amphetamine, procaine, prilocaine, lidocaine, bupivacaine, lignocaine, creatinine, and protamine. Organic anions sensed by this method include but not limited to salicylate, phthalate, maleate, and heparin. Neutral analytes sensed by this method include but are not limited to ammonia, ethanol, and organic amines. In an embodiment, ions that can be sensed include potassium, sodium, chloride, calcium, and hydronium (pH). In a particular embodiment, concentrations of both sodium and potassium are measured. In another embodiment, concentrations of both magnesium and potassium are measured.

Embodiments of the invention can include chemical sensing elements configured to detect a physiological analyte of interest by exhibiting a change in optical properties. In some embodiments, the physiological concentration of an analyte is detected directly. In other embodiments, the physiological concentration of an analyte is detected indirectly. By way of example, a metabolite of a particular analyte can be detected instead of the particular analyte itself. In other embodiments, an analyte can be chemically converted into another form, such as an ion, in order to make the process of detection easier. By way of example, an enzyme can be used to convert an analyte into another compound which is easier to detect.

In some embodiments, the chemical sensing element comprises a non-carrier or carrier-based fluorescent or colorimetric ionophoric composition that includes a complexing moiety for reversibly binding an ion to be analyzed, and a fluorescing or calorimetric moiety that changes its optical properties as the complexing agent binds or releases the ion. Aspects of exemplary chemical sensing elements are described in U.S. patent application Ser. No. 11/383,933, the content of which is herein incorporated by reference.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. An implantable medical device comprising:
   a housing defining an interior volume, the housing comprising a housing wall, the housing wall defining an aperture and further defining a stepped flange surrounding the aperture, the stepped flange including a recessed portion;
   an optical sensor assembly coupled to the housing wall, the optical sensor assembly occluding the aperture and welded to the recessed portion of the stepped flange; the optical sensor assembly comprising
      an electro-optical module, the electro-optical module comprising
         an optical excitation assembly;
         an optical detection assembly;
      a chemical sensing element, the chemical sensing element configured to detect a physiological analyte by exhibiting a change in optical properties; and
      an optical window disposed between the electro-optical module and the chemical sensing element, the optical window configured to allow the transmission of light between the electro-optical module and the chemical sensing element.

2. The implantable medical device of claim 1, the interior volume of the housing hermetically sealed off from the outside of the housing.

3. The implantable medical device of claim 1, further comprising a flange surrounding the edges of the optical window forming a hermetic seal between the flange and the optical window.

4. The implantable medical device of claim 1, further comprising an optical shroud disposed between the optical excitation assembly and the optical detection assembly.

5. The implantable medical device of claim 1, the optical sensor assembly welded to the housing.

6. The implantable medical device of claim 1, further comprising an infrared light filter disposed over the optical detection assembly.

7. The implantable medical device of claim 1, the optical window comprising a rigid planar optical window.

8. The implantable medical device of claim 1, further comprising
   a cover layer disposed over the chemical sensing element, the cover layer comprising a material permeable to the physiological analyte.

9. The implantable medical device of claim 8, wherein the cover layer is flush with an outside surface of the housing wall.

10. The implantable medical device of claim 8, wherein the cover layer is opaque.

11. The implantable medical device of claim 1, the optical excitation assembly comprising a plurality of light emitting diodes.

12. The implantable medical device of claim 1, the optical detection assembly comprising a plurality of photodiodes.

13. An implantable medical device comprising:
   a housing defining an interior volume, the housing comprising a housing wall, the housing wall defining an aperture;
   an optical sensor assembly coupled to the housing wall, the optical sensor assembly occluding the aperture; the optical sensor assembly comprising
      an electro-optical module, the electro-optical module comprising
         an optical excitation assembly;
         an optical detection assembly;
      a chemical sensing element, the chemical sensing element configured to detect a physiological analyte by exhibiting a change in optical properties wherein the optical sensor assembly is configured to be fitted within the aperture of the housing in only a single orientation; and an optical window disposed between the electro-optical module and the chemical sensing element, the optical window configured to allow the transmission of light between the electro-optical module and the chemical sensing element.

14. The implantable medical device of claim 13, the interior volume of the housing hermetically sealed off from the outside of the housing.

15. The implantable medical device of claim 13, further comprising a flange surrounding the edges of the optical window forming a hermetic seal between the flange and the optical window.

16. The implantable medical device of claim 13, further comprising an optical shroud disposed between the optical excitation assembly and the optical detection assembly.

17. The implantable medical device of claim 13, the optical sensor assembly welded to the housing.

18. The implantable medical device of claim 13, the optical window comprising a rigid planar optical window.

19. The implantable medical device of claim 13, further comprising an infrared light filter disposed over the optical detection assembly.

20. The implantable medical device of claim 13, further comprising:

a cover layer disposed over the chemical sensing element, the cover layer comprising a material permeable to the physiological analyte.

* * * * *